United States Patent [19]

Albertsson et al.

[11] Patent Number: 5,762,496
[45] Date of Patent: Jun. 9, 1998

[54] DISPOSABLE DENTAL SALIVA EJECTOR

[75] Inventors: Christer Albertsson, Eskilstuna; Matts Folkö, Köping; Bengt Mattsson, Uppsala, all of Sweden

[73] Assignees: Koping Industri-Plast AB, Koping; Dry Invent Bengt Mattsson AB, Uppsala, both of Sweden

[21] Appl. No.: 520,956

[22] Filed: Aug. 30, 1995

[30] Foreign Application Priority Data

| Sep. 2, 1994 | [SE] | Sweden | 9402926 |
| Mar. 17, 1995 | [SE] | Sweden | 9501025 |

[51] Int. Cl.$^6$ ............................................. A61C 17/10
[52] U.S. Cl. ............................................. 433/93; 433/94
[58] Field of Search ........................... 433/91, 93, 94, 433/95, 96

[56] References Cited

U.S. PATENT DOCUMENTS

| 1,202,264 | 10/1916 | Brown | 433/93 |
| 2,595,666 | 5/1952 | Hutson | 433/96 |
| 2,859,519 | 11/1958 | Colin | 433/93 |
| 3,101,543 | 8/1963 | Baughan | 433/94 |
| 3,324,855 | 6/1967 | Heimlich | 433/91 |
| 3,631,598 | 1/1972 | Lussier | 433/94 |
| 3,758,950 | 9/1973 | Krouzian | 433/91 |
| 3,787,978 | 1/1974 | Rogers . | |
| 3,928,916 | 12/1975 | Hansson | 433/91 |
| 4,017,975 | 4/1977 | Johnson . | |
| 4,325,695 | 4/1982 | Sundelin et al. | 433/91 |
| 4,906,188 | 3/1990 | Moseley | 433/93 |
| 5,015,184 | 5/1991 | Perry et al. | 433/91 |
| 5,071,347 | 12/1991 | McGuire | 433/91 |
| 5,094,616 | 3/1992 | Levenson | 433/91 |
| 5,151,094 | 9/1992 | Hanifi | 433/91 |
| 5,203,699 | 4/1993 | McGuire | 433/91 |

FOREIGN PATENT DOCUMENTS 2 059 780  10/1980  United Kingdom .

*Primary Examiner*—Cary E. O'Connor
*Attorney, Agent, or Firm*—Herbert Dubno; Yuri Kateshov

[57] ABSTRACT

A disposal dental saliva ejector with a suction part, at least one suction orifice in the suction part, a holder part and a curved intermediate part has a chin plate displaceably mounted on the holder part. The holder part defines a trough-shaped guiding channel for a duct and the chin plate has a mounting sleeve with a specifically shaped opening enabling the chin plate to occupy a central position and at least one lateral position, and to be temporarily fixed in a selected height position on the holder part.

17 Claims, 4 Drawing Sheets

DISPOSABLE DENTAL SALIVA EJECTOR

The invention relates to a disposable dental saliva ejector used in dental operations and which serves the double purpose of keeping the operational field in the oral cavity dry, and of pressing down and holding back the patient's tongue.

BACKGROUND OF THE INVENTION

A number of various dental saliva ejectors have become known and among them are disposable metal saliva ejectors in which the tongue holder is fixable by means of a screw in a mounting sleeve of the ejector (Swedish patents 143 632 and 163 702).

Another saliva ejector, described in U.S. Pat. No. 3,753,292 is not provided with a tongue holder and a chin plate but has a support frame made of metal or plastic with a connection base at one end and an open, i.e. trough-shaped, guide channel extending therefrom to a restraint loop at the other end. The guide channel comprises a curved part between the base and the loop and is somewhat more than semi-circular in cross-section, so that it can embrace and retain a flexible tubular conduit. It is also known (e.g. from U.S. Pat. No. 5,094,616) to cover the suction end made of a dental saliva ejector with a disposable element of soft plastic to protect the patient's oral cavity.

OBJECTS OF THE INVENTION

It is an object of the invention to provide a disposable saliva ejector made entirely of plastic, i.e. not comprising any metal components.

SUMMARY OF THE INVENTION

Saliva ejectors of this kind comprise a stem having a tubular section part to be introduced into the patient's oral cavity, a straight holder part and a curved intermediate part connecting the two aforesaid parts, the suction part being provided with at least one suction orifice and the holder part having a free end at which an evacuation tubing may be connected to the ejector. A tongue holder is attached to the suction part, a chin plate is displaceably mounted on the holder part and a duct means extends from the suction part to the lower free end of the holder part and there is adapted for connection with an evacuation tubing.

The ejector according to the invention is provided with a tongue holder, onto which a soft plastic element with filtering capacity may be slipped, as with an adjustable chin plate which may be positively fixed in a selected height position on the holder part, swung into at least one lateral position, and preferably temporarily locked in a lateral position.

According to the invention, the disposable dental saliva ejector comprises in combination:

a stem including a tubular suction part adapted to be introduced into the patient's oral cavity and provided with at least one suction orifice; a straight holder part with a free lower end; and a curved intermediate part interconnecting the suction and holder parts; all said three parts lying in one common plane;

a chin plate displaceably mounted on said holder part, and a duct means extending from the suction part to the said free lower end of the holder part and adapted to be there connected to an evacuation tubing.

The holder part of the stem has a trough-shaped guiding channel with an outer face and an inner face and in cross-section has the shape of a U with a curved central portion and two straight shanks, the guiding channel being adapted to receive the duct means and being limited by two longitudinal edges extending at a given mutual spacing.

The chin plate has a mounting sleeve with a non-circular inner sleeve opening by means of which it is slipped-on on the holder part, the sleeve opening having a first section with a curved portion having a radius of curvature which is equal to the radius of curvature of the outer face of the said curved portion of the holder part, which curved portion of the first section passes into two straight shanks having distant ends which are more spaced apart than the said longitudinal edges of the holder part. In a continuation of said first section, a second section has one lobe adjacent each of the said two shanks of the first section, and a back-up portion located between the two lobes.

The back-up portion has a breadth which is smaller than the spacing of the two longitudinal edges of the holding part, the back-up portion being limited by a concave limiting face.

The two lobes are adapted to receive the said longitudinal edges and the thereto adjacent portions of the holder part so as to enable the chin plate to occupy, besides of a central position, at least one swung-out lateral position.

The holder part and the mounting sleeve may be provided with co-operating, releasable locking means for temporarily locking the chin plate in a selected height position on the holder part, cooperating stop means defining at least one lateral position of the chin plate.

The co-operating stop means on the holder part and on the mounting sleeve can be adapted to releasably lock the chin plate in one of two opposite lateral positions.

Co-operating locking means for locking the chin holder in a selected lateral position can be provided on the holder part and on the mounting sleeve.

The duct means can be embodied by a resilient and flexible tube, an outer periphery of which has the same radius of curvature as the inner periphery of the curved portion of the holder part and the concave limiting face of the back-up portion, the distance between the limiting face and the said inner face of the holder part being less than twice the said radius, so that the tube is constantly compressed in the direction between the limiting face and the inner face. The height position locking means can comprise a plurality of transverse grooves provided at selected intervals on the outer face of the holder part and, at the inside of the inner sleeve opening, a projecting crest means adapted to fit into the said grooves. The crest means can be embodied by one single crest with a concave limitation and located at the curved portion of the inner sleeve opening or by one lateral crest with a rectilinear limitation located at the end of each shank of the inner sleeve opening and dimensioned so as to engage the grooves on the holder part only when the chin plate is in its lateral position. The height position locking means at the mounting sleeve can comprise at least one web at the inner end of each lobe, and a plurality of indents at selected intervals on said longitudinal edges, adapted to receive said web when the chin plate is swung-out into a lateral position. Further, the height position locking means can comprise a plurality of indents at selected intervals on said longitudinal edges of the holder part, and a resilient flap on the mounting sleeve, which flap is on its inner side provided with laterally located teeth engageable in said indents, and carries a handle arm on the outside. The resilient flap can be embodied by a part of the mounting sleeve which is separated from the rest of the mounting sleeve by two slots located between the first and the second section of the sleeve opening. The tongue holder can be attached to the suction part and can be embodied by a frame

3 structure which encompasses an inner frame space into which opens the suction orifice. The frame structure can comprise a plurality of limbs, and is adapted to bear a disposable filter element.

The tubular suction part can taper in the direction toward the suction orifice and embody a first limb of the said frame structure, the other limbs of which are non-hollow.

The frame structure can have the general shape of a rectangle with three rounded corners and one sharp corner. The filter element can be embodied by a flat filter bag which is closed on all sides with the exception of the side by which it is slipped-on on the frame structure. The frame structure can be provided with ribs defining a cage supporting the filter bag. The limbs extending from said first limb can taper in the direction away from the first limb. And the limb opposite the first limb can be cambered outward. If desired, the limb opposite the said first limb can slope in a direction away from the free end of the suction part. A plate can be attached to at least one of the limbs so as to occupy the inner frame space with the exception of at least an area adjacent the suction orifice. The plate can be attached to the said first limb and is detached at least from the limb opposite the first limb, so as to endow the frame structure with a degree of resilience in the direction of right angles to the longitudinal direction of the first limb.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
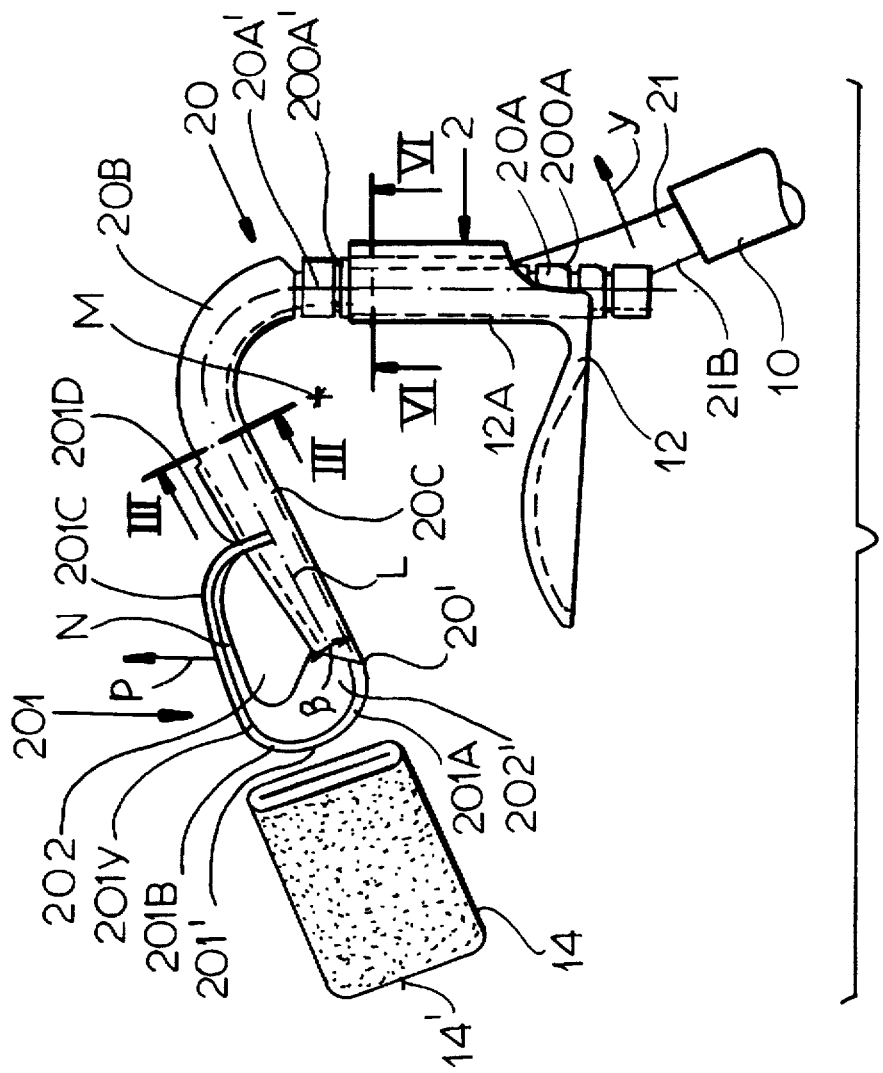
FIG. 1 is an elevational view of a preferred embodiment of the saliva ejector of the invention.
Figure 2:
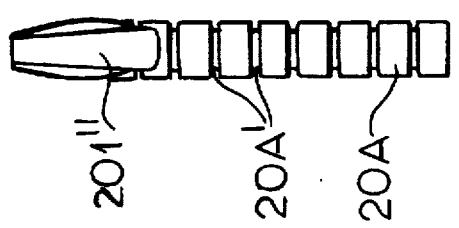
FIG. 2 is a lateral view of the stem of the ejector of FIG. 1.
Figure 4:
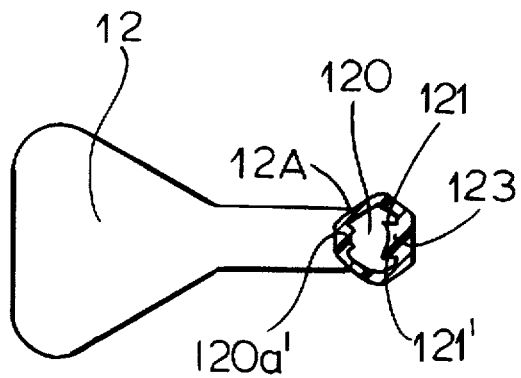
FIG. 4 is a plan view of a slightly modified embodiment of the chin plate of FIG. 1 on the scale of FIG. 1.
Figure 3:
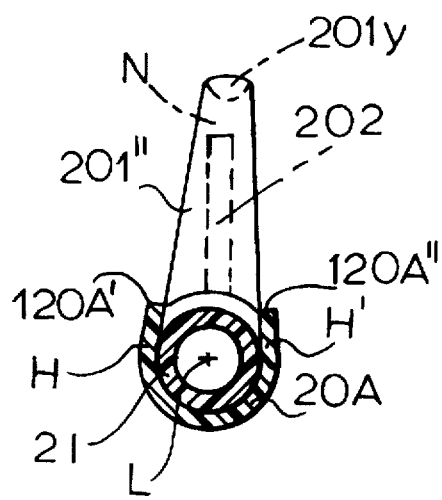
FIG. 3 is a cross-sectional view on a somewhat larger scale along the plane III—III in FIG. 1.

According to FIGS. 1 to 3, the saliva ejector of the invention comprises a rigid stem 20 which has a longitudinal axis L and which essentially includes a straight holder part 20A, a curved intermediate part 20B, and a distinctively shaped suction part 20C. All of the above-mentioned parts lie in one plane and the entire stem 20 is made in one piece of such plastic material as e.g. polypropene, or polyethylene, or of a decomposable starch-based polymer.

The holder part 20A and the intermediate part 20B have the shape of a trough limited by parallel longitudinal edges 120A', 120A" (FIG. 3). The trough is U-shaped in cross-section with two parallel shanks H. H', and is preferably open in the direction outwards the single bend of the intermediate part 20B, i.e. away from that part's center of curvature M. It may however in principle also be open in the reverse direction.

The suction part 20C defines an extension of the intermediate part 20B, but is tubular instead of trough-shaped, and tapers toward its free end provided with a suction orifice 20' and running into a frame structure 201. The frame structure 201 comprises three massive non hollow limbs 201', 201y, 201" defining an inner frame space. The frame structure 201, onto which a filter element 14 may be slipped, extends in the plane of the stem 20, projects away from the stem's longitudinal axis L in the opposite direction than where the said center of curvature M lies, and has the generally a shape of rectangle whose first limb is essentially embodied by the suction part 20C itself. The limbs of the frame structure 201 are interconnected by three rounded corners 201A, 201B, 201C and one sharp corner 201D. Viewed in a plane at right angles to the drawing plane of FIG.1, the outer limb 201' and the inner limb 201" taper in the direction away from the first limb (suction part 20C), as is best seen in FIGS. 2 and 3.

The suction orifice 20' opens toward the inner frame space, i.e. away from the bottom of the patient's mouth. The area of the suction opening 20' may be selected within certain limits by selecting the angle β relative the longitudinal axis L under which the tubular suction part 20C is terminated.

The inner frame space may be occupied, with the exception of at least an area 202' adjacent the suction orifice 20', by a plate 202 which is affixed to at least one of the frame limbs, preferably to the suction part 20C, as shown in the drawing. The plate 202 is preferably detached from the frame structure 201 adjacently at least one of the other limbs, such as at N adjacently the upper limb 201y, in order to endow the frame structure 201 with some degree of resilience.

The upper limb 201y may be cambered outwards, as indicated by the arrow p, and may slope in the direction towards the inner limb 201". The frame structure 201 is, like the rest of the stem 20, made of plastics. The partial detachment of the plate 202 and the cambering of the limb 201y provides secure temporary retainment of the filter element on the frame structure 201 When the latter is slipped on, and at the same time is readily removable after use.

The filter element 14 has in the illustrated exemplary embodiment a flat bag shape which is open only along one side defining its inner edge which is slipped on the frame structure, and which otherwise is fully sealed even along its outer edge 14'. Preferably, at least the two of its outer corners at the said outer edge 14' are rounded-of or chamfered. When placed on the frame structure 120, the filter bag is closed along three sides which lie adjacent the lower, the outer and the upper limbs of the frame structure 201.

Figure 5:
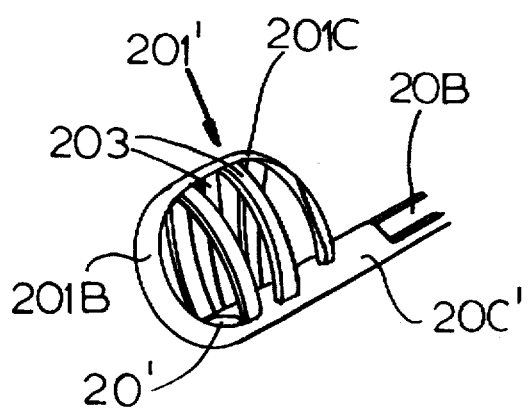
FIG. 5 is a perspective view of an alternative embodiment of the frame structure of the tongue holder.

In FIG. 5 is shown a frame structure 201' provided with outwardly cambered ribs 203 defining a cage which holds the walls of the filter bag 14 apart.

According to the present invention, the suction part 20C and the frame structure 201, 201' projecting therefrom are merged into to distinctively shaped tongue holder including the plate 202 and/or the filter and essentially extending essentially in the plane of the stem 20 (i.e. the drawing plane of FIG. 1).

The stem 20 receiving a flexible, and at least to some degree resilient, hose or tube 21 which defines a duct means extending from the suction part 20C to the lower free end of the holder part 20A.

The upper end 21A of the tube 21 is in any known and suitable manner, e.g. by bonding, affixed in the tubular suction part 20C, and the rest of the tube 21 reposes in the trough of the intermediate and holder parts. The lower end 21B of the tube 21 projects from the holder part 20A and may be in any known manner connected to an evacuation hose or tube 10 leading to a suction device, not shown.

A chin plate 12, defining a fixation means of the saliva ejector, is with the aid of a mounting sleeve 12A slidably, and to a limited extent rotatably mounted, i.e. slipped-on, on the holder part 20A. Upon application, the saliva ejector rests with the lowermost portion of its suction part 20C, which generally is covered by the soft filter bag 14, on the bottom of the patient's mouth, and the chin plate 12 is brought into an operational position by being moved upwards from a lowermost position on the holder part 20A and, when the best fixing position has been reached, is locked in place by being swung into a lateral position.

This adjustment movement of the chin plate must be easy to perform and the chin plate must be reliably fixed in the selected height position, being at the same time readily releasable.

In order to define a selected height position of the chin plate 12, the holder part 20A of the ejector stem 20 is on its outer face at selected intervals provided with transversal grooves 20A' (FIG. 1) and/or with indents 200A, and the mounting sleeve 12A of the chin plate 12 is provided with co-operating engagement'means, exemplary embodiments of which are described more in detail below.

In order to allow the chin plate to be turned or swung from a central position into at least one lateral or side position, the inner opening 120 in the mounting sleeve 12 has a particular shape adapted to co-operate with the holder part 20A of the stem 20. Preferably, the possibility is provided to swing the chin plate into one of two possible lateral positions. Also preferably, means (snap-in means) for releasably locking the chin plate in the lateral position are provided.

Figure 6:
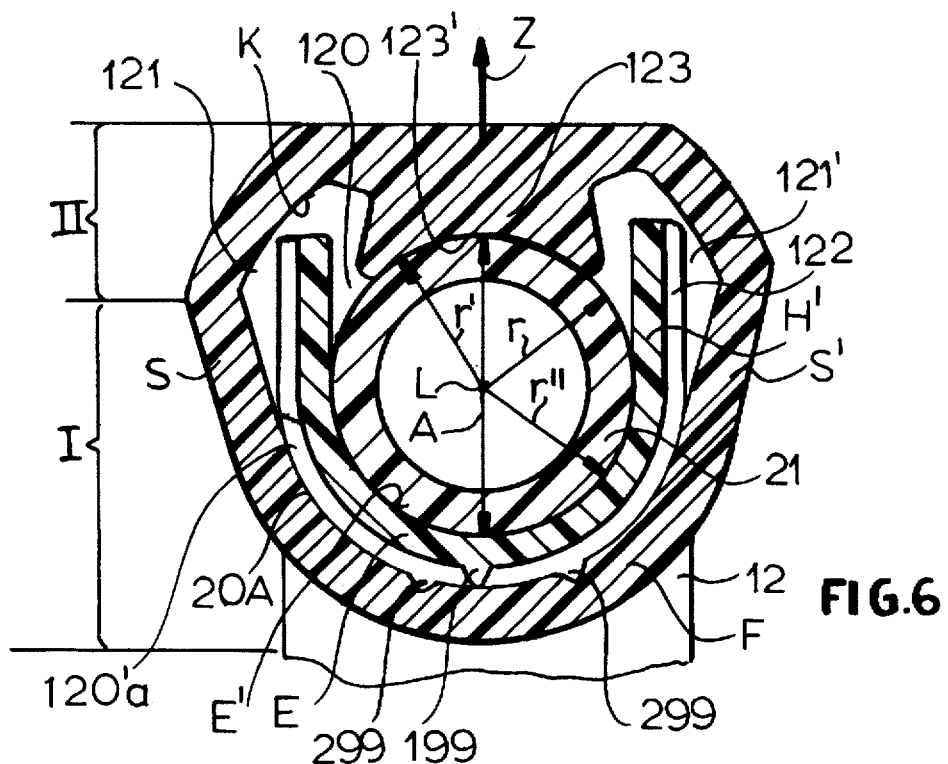
FIG. 6 is a cross-sectional view on a considerably larger scale along the plane VI—VI in FIG. 1 through a first embodiment of the mounting sleeve of the chin plate and through the holder part of the stem, the chin plate being in its central position.

According to FIG. 6, the inner opening (sleeve opening) 120 of the mounting sleeve 12A has a distinctive shape comprising a first section I with an essentially circular portion F and two diverging, straight shanks S, S', and a second section II which comprises two lateral lobes 121, 121' separated by a central back-up portion 123. The inner opening 120 has thus the shape of a letter U with diverging shanks S, S' which pass into the two lateral lobes 121, 121'.

The back-up portion 123 is limited by a concave contact face 123' and has a breadth B (FIG.7) which is smaller than the mutual spacing C of the shanks H, H' of the holder part 20A, i.e. of the longitudinal edges 120A', 120A" of the holder part 20A.

The tube 21 has in cross-section a radius r, and as well the contact face 123', as the inner face E' of the curved part E in the holder part 20A, have essentially the same radius of curvature r', r".

The shape of the outer limitation of the lobes 121, 121', in continuation of the U-shaped portion, such as at K is functionally irrelevant, and may be selected only with regard to a suitable outer shape of the mounting sleeve 12A.

The co-operating engagement means at the mounting sleeve 12A may in a first embodiment, shown in FIG. 6, be defined by a concave crest 120' a which for clarity is not shown in section and which is located at the inside of the curved portion F of the opening 120, being adapted to engage the grooves 20A' on the outer face of the holder part 20A. The crest 120' a occupies a sector of approximately 150° as seen from the longitudinal axis L.

The distance A between the contact face 123' of the back-up portion 123 and the inner face E' of the curved portion E of the holder part 20A is somewhat smaller than the outer diameter (=2r) of the flexible tube 21. The tube 21 in the mounting sleeve 12 is thus slightly compressed in the direction A, and as it tends to resume its undeformed shape, urges the back-up portion 123 outwardly in the sense of arrow z. Consequently, the curved portion F of the mounting sleeve 12 is pushed towards the curved portion E of the holder part 20A, and the crest 120'a is pushed into an adjacent groove 20A'

This effect is still enhanced by the fact that the evacuation tubing 10 tends to bend the inserted tube 21 outwardly in the sense of arrow y (FIG. 1) when the ejector is in use.

The chin plate 12 may be by hand moved up and down the holder part 20A, the crest 120'a snapping from one groove 20A' to another, and the mounting sleeve 12A being possibly pressed in the sense of arrow q (FIG.1). In the embodiment of FIG. 6, the chin plate 12 is thus retained in its selected height position by engagement of the crest 120'a in one of the grooves 20A'.

Figure 7:
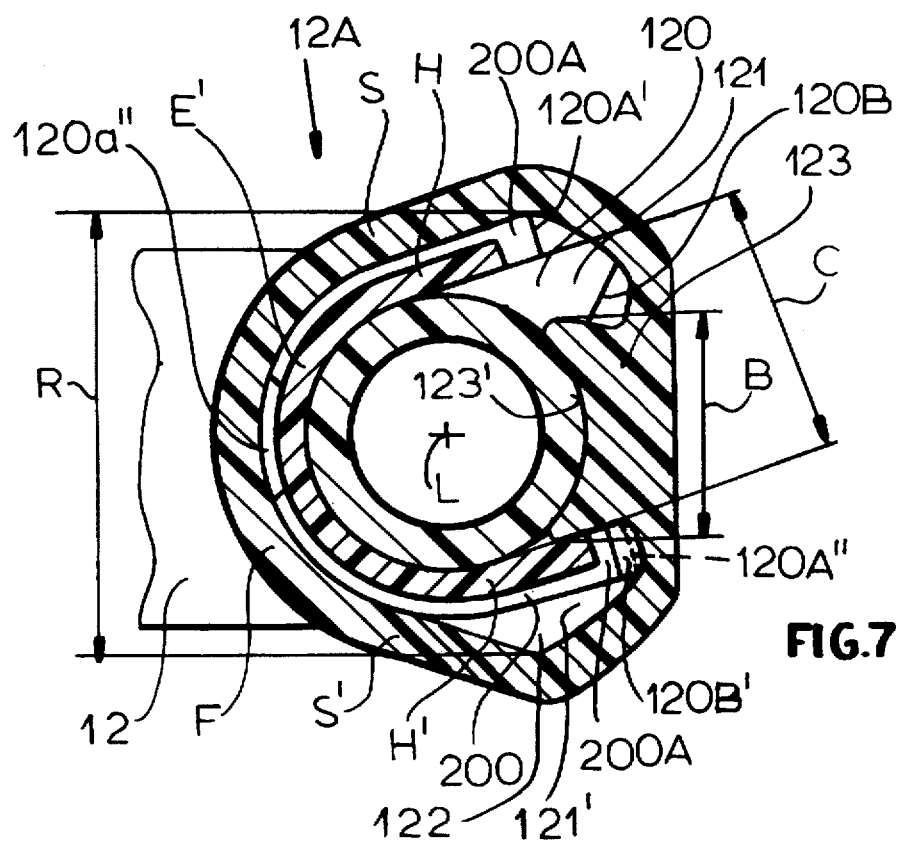
FIG. 7 is a similar cross-sectional view through a second embodiment of the mounting sleeve, the chin plate being in one of its lateral positions.

The central position of the chin plate 12 is the position in which the chin plate extends symmetrically on both sides of the plane of the stem 20 (i.e. the drawing plane of FIG. 1). For changing this central position into a lateral one, the chin plate is pushed aside so long as stop means allow, i.e. untill one of the shanks S, S' of the opening 120 bears against the adjacent shank H, H' of the holder part 20A, and/or one of the edges 120A', 120A" comes to bear against, or at least to lie closely adjacent, the innermost end of one of the lobes 121, 121', as shown in FIG. 7.

The stop means may preferably be complemented by locking means which temporarily locks the chin plate in the selected lateral position. Such locking means can be embodied by any suitable snap-in means or other means known for the purpose. In the example shown in FIG. 6 comprise this means an axially extending crest such as 199 on one of the holder part or mounting sleeve (the holder part in the illustrated embodiment) and corresponding grooves such as 299 in the other part (the mounting sleeve in the illustrated embodiment). The inherent resilience of the tube 21 will press the longitudinal crest into the longitudinal groove lying opposite.

It will be appreciated that the general condition for the sideward motion of the chin plate 12 is that the spacement R (FIG.7) between the distant (i.e. distant from the curved part) ends of the shanks S, S' of the inner opening 120 in the mounting sleeve 12A is larger than the spacement C between the ends of the shanks H, H' of the holder part 20A (i.e. between its longitudinal edges 120A', 120A"), and that at the same time the breadth B of the back-up portion 123 is smaller than the spacing C.

This condition does not necesserily demand that the shanks H H' extend parallel. It includes several other alternatives, e.g. those in which the shanks S, S' are parallel and the shanks H, H' are convergent, or the shanks S, S' are convergent and the shanks H, H' still more convergent (the tube 21 being flexible and resilient, it may be squeezed even into a channel with tapering side walls).

It will be readily recognised that the degree to which the shanks S, S' in the mounting sleeve diverge more (or converge less) than the shanks H, H' of the holder part, defines the lateral positions of the chin plate, e.g. to ±150° relative the central position.

In the second embodiment according to FIG. 7 is the crest 120'a of FIG.6 complemented by webs 120B, 120B' provided in both lobes 121, 121' at their innermost ends, and by indents 200A (FIG. 1), adapted to receive these webs, in the edges 120A', 120A".

The indents 200A have the same mutual spacing as the grooves 20A' and are preferably, but not necessarily, located at both ends of these grooves, as shown in FIG. 7.

The chin plate 12 may in its central position be moved up and down the holder part 20A in the same manner as described before, and is locked in a selected indent 200A (groove 20A) by being turned into one of its lateral positions, so that the respective web 120B, 120B' becomes engaged in one of the indents 200A. For disengaging, the chin plate 12 is again turned into the central position. The above mentioned snap-in means releasably secure the chin plate in the lateral position.

If stronger fixation is desired, the webs 120B, 120B' may be provided in several tiers. The centrally located crest 120"a may in this instance be shorter than in the embodiment of FIG. 6, or it may be entirely omitted. It will be understood that even the webs 120B, 120B' may be entirely substituted by the crest 120'.

Figure 8:
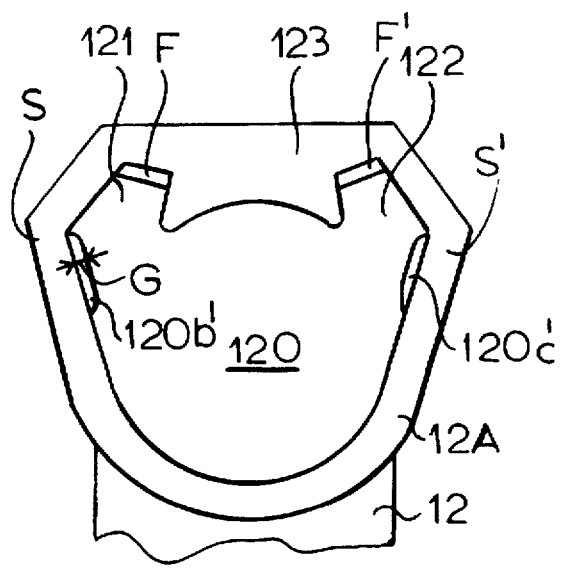
FIG. 8 is a plan view of a fourth embodiment of the mounting sleeve.

In a third embodiment according to FIG. 8 is the single centrally located crest 120'a, 120"a substituted by two lateral crests 120'b, 120'c, each located at one end of the U-shaped portion of the inner opening 120. These crests 120'b, 120'c have such dimensions, chiefly a width G, as to engage the grooves 20A' when the chin plate 12 is in one of its lateral positions, but not when it is in its central position.

Figure 11:
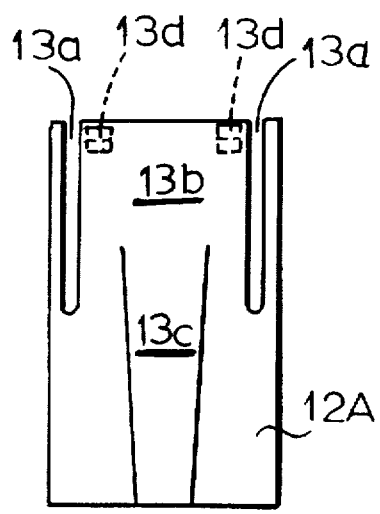
FIG. 11 is a lateral in the sense of arrow XI in FIG. 10 of the mounting sleeve of FIGS. 9 and 10.
Figure 10:
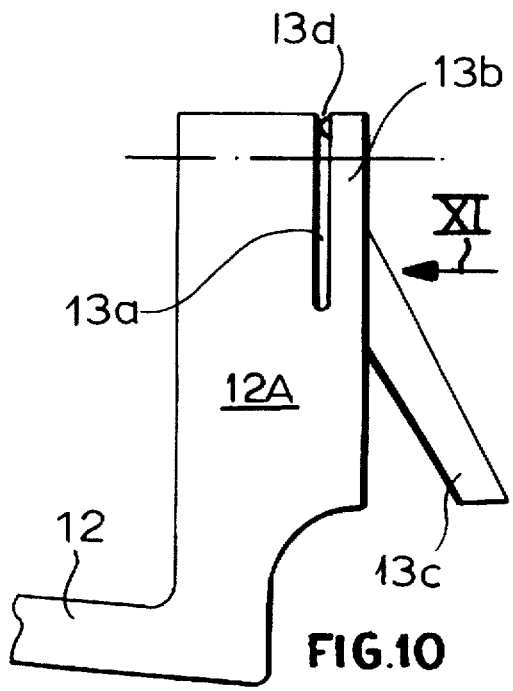
FIG. 10 is a lateral view in the sense of arrow X in FIG. 9; of the mounting sleeve of FIG. 9.
Figure 9:
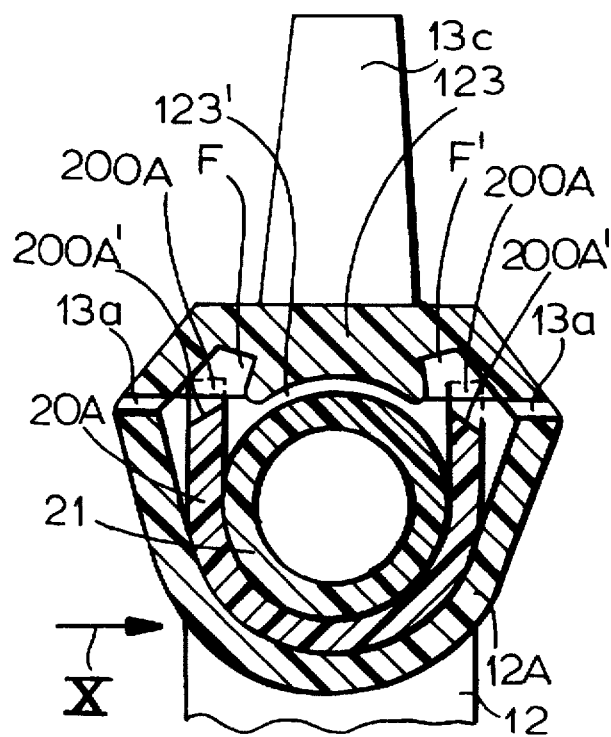
FIG. 9 is cross-sectional view through a fifth embodiment of the mounting sleeve of the chin plate and through the holder part of the stem, the chin plate being in its central position.

In a fourth embodiment according to FIGS. 9 to 11 is a part 13b of the mounting sleeve 12A separated from the rest of the mounting sleeve by two slots 13a which are situated at the transition between the U-shaped portion of the opening 120 and the two lobes 121, 121'. Said part 13b embodies a resilient flap, carries laterally on the inside of its free end two engagement teeth 13d, and has a handle arm 13c which projects obliquely from the outside.

The webs 120B, 120B' extend in this embodiment essentially so far as to the contact face 123' of the back-up part 123, and the indents 200A are deeper than in the embodiment of e.g. FIG. 8. The inner limitations 200A' (FIG. 9) of the indents are chamfered outwards, so that the teeth 13d cannot prevent the chin plate 12 from being turned into its lateral positions.

The teeth 13d snap-in in the indents 200A when the chin plate is in its central position. When the outer end of the handle arm 13c is depressed, the free end of the flap 13b is lifted and the teeth 13d are disengaged.

In contrast to the previously described embodiments, the chin plate 12 may be locked on, as disengaged even in its central position.

The saliva ejector of the invention may be as a whole, i.e. the stem with the inserted tube and with the chin plate, discarded as normal "all plastic" refuse. Only the filter bag, which possibly may contain amalgam chips or the like, has to be removed from the tongue holder and discarded as "perilous" refuse.

We claim:

1. A disposable dental saliva ejector comprising:

longitudinal duct means for evacuating saliva from a patient's oral cavity;

a stem receiving said duct means and including:

a tubular suction part adapted to be introduced into the oral cavity and provided with at least one suction orifice, a straight holder part spaced downstream from said tubular part and having a free lower end, said holder part being provided with a guide channel having a U-shaped cross-section and formed by a pair of straight shanks and a curved bottom having a radius and bridging said shanks, said shanks and said bottom being formed with inner and outer sides forming respectively an inner and outer face of said holder part, said inner sides of said shanks being spaced apart at a distance, and a curved intermediate part connecting said suction and holder parts and lying in a common plane therewith, said duct means extending from said suction part to said free lower end of said holder part;

a chin plate provided with a mounting sleeve mounted displaceably on said holder part of said stem, said mounting sleeve being formed with:

a respective curved part formed with a radius of curvature equal to said radius of said curved bottom of said holder part and juxtaposed therewith in a mounting position, two straight parts bridged by said curved part and having respective ends remote from said curved part spaced apart at a distance greater than said distance between inner sides of the shanks of the holder part, a pair of lobes running towards one another from said ends of said straight parts and into a back-up portion bridging said lobes, said back-up portion being smaller than said distance between the inner sides of the shanks of the holder part and being formed with an inner concave face juxtaposed with said duct means, said chin plate being rotatable on said holder part from said mounting position to at least one lateral position; and locking means for arresting sliding of said chin plate along said stem in a selected height position of said chin plate and for releasably interlocking said chin plate and said holder part of said stem in said one lateral position.

2. The saliva ejector defined in claim 1 wherein said chin plate is rotatable in opposite senses on said holder part from said mounting position to two lateral positions, said stop means securing said chin plate in said two lateral positions.

3. The saliva ejector defined in claim 1 wherein said duct means includes a flexible resilient tube mounted compressed between said curved bottoms of said guide channel of the holder part and said inner concave face of said mounting sleeve of said chin plate.

4. The saliva ejector defined in claim 1 wherein said locking means includes a plurality of transverse grooves formed in said outer face of said holder part and crest means formed on said mounting sleeve and projecting inwardly toward said outer face of said holder part to engage a respective one of said transverse grooves.

5. The saliva ejector defined in claim 4 wherein said crest means includes a single crest formed on said curved part of said mounting sleeve and having a concave inwardly projecting limiting face facing said grooves on said holder part.

6. The saliva ejector defined in claim 4 wherein said crest means includes two crests, each of said crests being formed on a respective one of said straight parts of the mounting sleeve and having a rectilinear inwardly projecting limiting face engaging said groves when in said lateral position.

7. The saliva ejector defined in claim 1 wherein said locking means includes at least two webs each formed on the respective one of said lobes of said mounting sleeve and a plurality of indents formed at selected intervals on said inner sides of straight shanks of said holder part and adapted to receive said webs in said lateral position.

8. The saliva ejector defined in claim 1 wherein said locking means includes a plurality of indents formed on said shanks of said holder part and spaced apart at selected intervals, and a resilient flap formed on the mounting sleeve, said flap being formed with teeth extending laterally from an inner side of said flap and with a handle arm formed on an outer side of said flap, said teeth being engageable with said indents in said lateral position, said mounting sleeve being formed with two slots each formed between the respective lobe and the straight part.

9. A disposable dental saliva ejector comprising:
a tubular suction part adapted to be introduced into an oral cavity of the patient and provided with at least one suction orifice formed at an end of said suction part;
a tongue holder attached to said suction part and formed with a frame including a plurality of limbs defining a frame space therebetween, a first one of said limbs being attached to said suction part and extending outwardly arcuately from an end of said suction part, the other limbs projecting laterally from said suction part and outwardly cambered from said one limb, said at least one suction orifice being open into said frame space.

10. The saliva ejector defined in claim 9 wherein said frame has a rectangular shape with three rounded corners and one sharp corner.

11. A disposable dental saliva ejector comprising:
a tubular suction part adapted to be introduced into an oral cavity of the patient and provided with at least one suction orifice formed at an end of said suction part;
a tongue holder attached to said suction part and formed with a frame including a plurality of limbs defining a frame space therebetween, a first one of said limbs being embodied by said suction part and the other limbs protecting from said suction part, said at least one suction orifice being open into said frame space; and
a disposable flat filter element formed with one side open to be slipped on said frame.

12. A disposable dental saliva ejector comprising:
longitudinal duct means for evacuating saliva from a patient's oral cavity;
a stem receiving said duct means and including:
a tubular straight suction part extending along a longitudinal axis and adapted to be introduced into the oral cavity and having a free end formed with an area extending at an angle to said longitudinal axis, said free end being formed with a suction orifice defined by said area;
a trough-shape straight holder part spaced downstream from said tubular part and having a free lower end, said holder part being provided with a guide channel, and
a trough-shaped intermediate part curved in a single bend and connecting said suction and holder parts and lying in a common plane therewith, said duct means extending from said suction part to said free lower end of said holder part, and
a tongue holder attached to said suction part and formed with a frame formed by a plurality of limbs which includes:
a pair of limbs extending in opposite directions, one of said pair of limbs being embodied by said suction part, and
the rest of said plurality of limbs projecting from said suction part and defining a frame space therebetween, said suction orifice being open into said frame space.

13. The saliva ejector defined in claim 12 wherein a disposable filter element in the form of a flat filter bag with one side open is slipped on said frame.

14. A disposable dental saliva ejector comprising:
a tubular suction part extending along a longitudinal axis and adapted to be introduced into the oral cavity and formed with a suction orifice;
a tongue holder attached to said suction part and formed with a frame formed by a plurality of limbs which includes:
a pair of limbs extending in opposite directions, said suction part running into one of said pair of limbs, and
the rest of said plurality of limbs projecting from said suction part and defining a frame space therebetween; and
a plate received within said frame space and mounted on said one limb of said pair and terminating next to the suction orifice, the plate having a free end terminating in the frame space.

15. The saliva ejector defined in claim 14 further comprising a filter slipped on said frame, said plate being detached from the other limb of said pair of limbs to reinforce the frame structure in a direction perpendicular to the longitudinal axis of said suction part by securing temporary retainment of said filter on said frame.

16. The saliva ejector defined in claim 14 wherein the other limb of said pair of limbs being chambered outward.

17. A disposable dental saliva ejector comprising:
a longitudinal stem including a tubular straight suction part extending along a longitudinal axis and adapted to be introduced into the oral cavity, and
a straight holder part spaced downstream from said tubular part and having a free lower end, said holder part being provided with a guide channel;
a chin plate provided with a mounting sleeve mounted rotatable between two predetermined opposite angular positions in and longitudinally slidable on said holder part;
cooperating locking means in said mounting sleeve and on said holder part for releasably arresting sliding of said chin plate along said stem in a selected height position of said chin plate selected from a plurality of predetermined discontinuous height positions; and
cooperating stop means on said holder part and in said mounting sleeve for arresting rotation of said chin plate in either of said two predetermined angular positions.

\* \* \* \* \*